(12) United States Patent
Dmuschewsky et al.

(10) Patent No.: US 9,855,059 B2
(45) Date of Patent: Jan. 2, 2018

(54) HOLDER FOR A MEDICAL, IN PARTICULAR A SURGICAL INSTRUMENT

(71) Applicant: WALDEMAR LINK GmbH & Co. KG, Hamburg (DE)

(72) Inventors: Klaus Dmuschewsky, Hamburg (DE); Amos Balzarini, Norderstedt (DE); Dörte Freisberg, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 70 days.

(21) Appl. No.: 14/413,720

(22) PCT Filed: May 24, 2013

(86) PCT No.: PCT/EP2013/060736
§ 371 (c)(1),
(2) Date: Jan. 9, 2015

(87) PCT Pub. No.: WO2014/016011
PCT Pub. Date: Jan. 30, 2014

(65) Prior Publication Data
US 2015/0141160 A1    May 21, 2015

(30) Foreign Application Priority Data
Jul. 24, 2012   (EP) ..................................... 12177714

(51) Int. Cl.
*A61B 17/16* (2006.01)
*A61B 17/00* (2006.01)

(52) U.S. Cl.
CPC .... *A61B 17/162* (2013.01); *A61B 2017/0046* (2013.01); *A61B 2017/00477* (2013.01); *A61B 2017/00862* (2013.01)

(58) Field of Classification Search
CPC ... B25G 3/10; B25G 3/12; B25G 3/18; B25G 3/20; B25G 3/24; A61B 2017/0046;
(Continued)

(56) References Cited

U.S. PATENT DOCUMENTS 2,784,987 A    3/1957  Corcoran
3,372,950 A *  3/1968  Wind ..................... B60K 37/00
                                                   403/326
(Continued)

FOREIGN PATENT DOCUMENTS

DE    2909469    7/1980
DE    10357104   7/2005
(Continued)

*Primary Examiner* — Matthieu F Setliff
(74) *Attorney, Agent, or Firm* — Sand & Sebolt

(57) ABSTRACT

A holder for a medical instrument having a quick coupling for receiving a connection end of the instrument's shaft. The quick coupling has a first coupling element having a first axial through-hole for the connection end and a second coupling element having a second axial through-hole for the connection end. The second coupling element is movable relative to the first coupling element in a direction crosswise to the axial direction of the through-holes from a locked position, in which the through-holes are offset so that an edge of the second through-hole engages behind an undercut on the shaft's connection end in a locking manner, to a release position, in which the through-holes lie in alignment and the connection end is freely guidable through both through-holes. A spring bridge connects the first and second coupling elements together and preloads the first and second coupling elements into the locked position.

20 Claims, 6 Drawing Sheets

(58) Field of Classification Search
CPC .......... A61B 2017/00464; A61B 2017/00473; A61B 2017/00477; Y10T 16/469; Y10T 16/4713; Y10T 403/1649; Y10T 403/1658; Y10T 403/1666; Y10T 403/1674; Y10T 403/30; Y10T 403/59; Y10T 403/591; Y10T 403/595; Y10T 403/599; Y10T 403/60; Y10T 403/606; Y10T 403/7039; Y10T 403/7062; Y10T 16/476; F16D 1/10; F16D 1/108; F16B 7/22; F16B 7/105; F16B 7/04; F16B 7/0406; F16B 7/0413

See application file for complete search history.

(56) References Cited

U.S. PATENT DOCUMENTS

| | | | | |
|---|---|---|---|---|
| 3,851,984 A * | 12/1974 | Crippa | ................. | A61C 17/02 15/176.6 |
| 4,224,786 A * | 9/1980 | Langlie | ................. | A01D 7/00 403/361 |
| 4,409,866 A * | 10/1983 | McBride | ................. | B25G 1/04 16/429 |
| 4,581,961 A * | 4/1986 | Lai | ................. | B25G 3/18 81/438 |
| 5,168,693 A * | 12/1992 | Ingyardsen | ................. | B25G 3/18 403/289 |
| 5,816,633 A * | 10/1998 | Odom | ................. | A01B 1/00 172/375 |
| 6,139,214 A | 10/2000 | Zirps et al. | | |
| 6,315,488 B1 * | 11/2001 | Parker | ................. | A01B 1/227 403/326 |
| 7,373,860 B1 * | 5/2008 | Rinner | ................. | B25G 1/105 16/430 |
| 7,904,987 B2 * | 3/2011 | Bayon | ................. | A47L 13/17 15/104.94 |
| 2006/0090301 A1 * | 5/2006 | Hsieh | ................. | B25G 1/105 16/430 |
| 2006/0254398 A1 * | 11/2006 | Ward | ................. | B25G 3/24 81/487 |
| 2007/0017072 A1 * | 1/2007 | Serio | ................. | A47L 13/42 24/573.11 |
| 2008/0244846 A1 * | 10/2008 | Bayon | ................. | A47L 13/17 15/104.94 |
| 2011/0030225 A1 * | 2/2011 | Wang | ................. | B25G 3/18 30/340 |
| 2012/0159794 A1 * | 6/2012 | Vogel | ................. | B25G 3/18 30/340 |

FOREIGN PATENT DOCUMENTS

| | | | | |
|---|---|---|---|---|
| DE | 602004001063 | 12/2006 | | |
| EP | 0893097 | 1/1999 | | |
| EP | 1943966 | 7/2008 | | |
| GB | 1441608 A * | 7/1976 | ......... | A61B 17/3213 |
| GB | 2403448 A * | 1/2005 | ............... | B25G 3/18 |

* cited by examiner

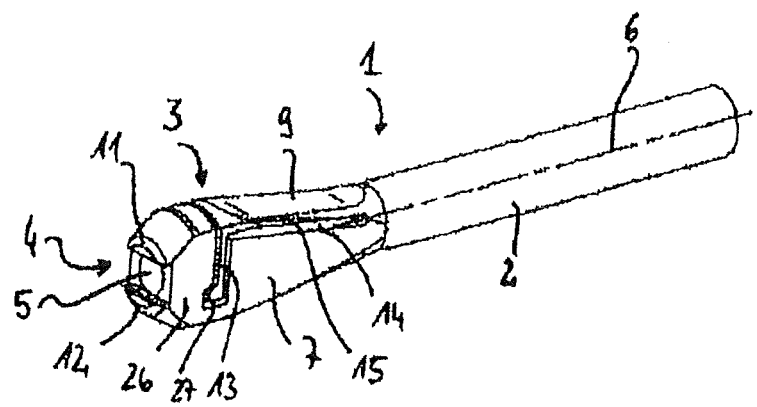
FIG. 1
FIG. 2
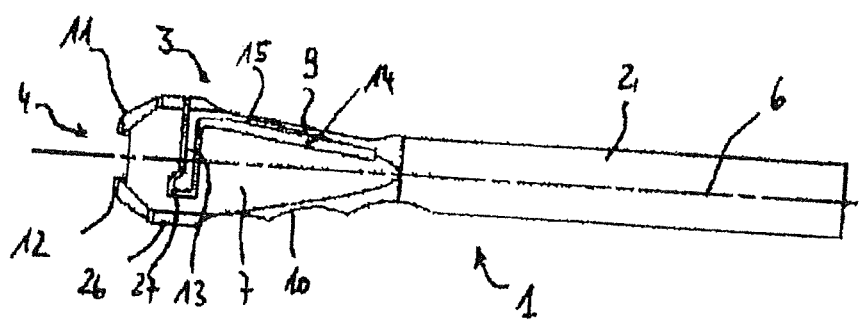

HOLDER FOR A MEDICAL, IN PARTICULAR A SURGICAL INSTRUMENT

TECHNICAL FIELD

The present invention relates to a holder for a medical, in particular a surgical instrument having a quick coupling for receiving a connecting end having an undercut on an instrument shaft of the medical instrument, wherein the quick coupling has a first coupling element having a first axial through-hole for the connecting end.

Such a holder serves to secure a medical instrument, which is held at least axially, for its use. It may be secured axially in such a way as to permit an axial play between the holder and the instrument while still holding the instrument securely on the holder without it being released unintentionally from the holder in the axial direction. In many cases, forces must be transferred with the holder not only in the axial direction but also for a rotary drive of the medical instrument—whether said forces are applied manually or are created by a motor drive. In such cases, with corresponding holders, means for a rotation-proof accommodation of the medical instrument and connection of same to the holder are also additionally provided with corresponding holders.

A medical instrument in the sense of the present description and invention may be in particular a tool that is used medically, such as a drill, a mill, a hasp, an awl, a saw or the like. However, a surgical instrument is also to be understood here to include components of implants or complete implants, whether they are implants as parts of prostheses, in particular including endoprostheses, or other implants to be connected to a holder for handling of same in setting, removing or adjusting or other steps.

PRIOR ART

A generic holder is described in DE 60 2004 001 063 T2, for example, where FIG. 1 shows, as an example of a medical instrument, a reamer, which has on one connecting end of its instrument shaft, labeled with reference numeral 78 there, a connecting configuration, which is referred to as a Hudson connector or as a Trinkl adapter that is inserted into a quick coupling of a holder for securing it there, said holder being secured in the manner of a clamping chuck with clamping claws that engage in an undercut on the connecting end of the instrument shaft by screwing on a clamping sleeve. FIG. 4 of this publication shows an alternative embodiment in which the connecting end of the instrument shaft is locked by means of locking balls.

Additional approaches that connect a shaft-type holder to surgical instruments in some other way are disclosed in EP 0 893 097 A2 and in DE 29 09 469 B1.

In particular when—as is usually customary with such holders—such holders with a medical instrument arrangement thereon are used in the course of a surgical procedure, typically not only the medical instrument itself but also the holder, in particular the region of the quick coupling, becomes soiled with blood and other body fluids, tissue constituents, bone chips and splinters or the like, for example, that are released during surgery. Such holders are not usually intended for a single use but instead are intended to be reusable equipment, so before they can be reused, they must be cleaned and sterilized after each use. A special challenge for cleaning and complete sterilization in particular is posed by the small parts contained in the known quick couplings of holders described previously and in particular also the gaps and spaces of small dimensions between such parts. If such quick couplings of the holders are designed to be dismantlable, then the personnel responsible for the cleaning and sterilization here must not only dismantle these quick couplings but must also handle them carefully for cleaning and sterilization and then reassemble them again rapidly afterward. However, if the quick couplings cannot be dismantled, it is often impossible to completely clean and sterilize small and very small gaps and interspaces, such as those which occur in the area of the seating of locking balls, for example, where there is always the possibility of dangerous concentration of contaminating residues, which can lead to complications in subsequent use of the holder as part of another medical procedure.

DESCRIPTION OF THE INVENTION

Therefore, the object of the present invention is to improve upon a known and generic holder for a medical, and in particular a surgical instrument, so that it has a simplified design in comparison with traditional holders and is easy to clean and to sterilize in the usual after-care.

This object is achieved by a holder for a medical, in particular a surgical instrument having a quick coupling for accommodating a connecting end having an undercut on an instrument shaft of the medical instrument, wherein the quick coupling has a first coupling element having a first axial through-hole for the connecting end, characterized in that the quick coupling has a second coupling element having a second axial through-hole for the connecting end, which second coupling element is movable relative to the first coupling element in a direction transverse to the axial direction of the through-holes out of the locking position, in which the first and second through-holes are offset relative to one another in such a manner that one edge of the second through-hole engages lockingly in the undercut on the connecting end of the instrument shaft, into a release position, in which the first axial through-hole and the second axial through-hole are aligned at least to such an extent that the connecting end can be passed freely through the two through-holes, wherein the first coupling element and the second coupling element are connected to one another in one-piece design via a spring bridge, and the spring bridge pre-stresses the first coupling element and the second coupling element into the locking position relative to one another. Advantageous refinements of such a holder include that the quick coupling has locking structures for cooperating with mating structures on the connecting end of the instrument shaft for a twist-proof arrangement of the instrument in the holder. The holder may include an exterior front side of the first coupling element and the quick coupling has side jaws that are arranged on opposite sides of the through-hole, passing through the surface on the front side and protruding outward from the surface on the front side on opposing sides of the side jaws, having mutually parallel planar contact surfaces facing one another for contact on the mating surfaces that form the opposing structures on the connecting end of the instrument shaft. The quick coupling has a base body on which the first coupling element and the second coupling element are integrally molded, a recess being provided in the base body and bordered by a wall of the base body on one end, with the spring bridge extending on a side opposite the wall and the second coupling element extending at an angle to the former. Additionally, the recess is shaped at an angle. The recess has a setback, and the second coupling element has a protrusion, together forming a stop, which prevents any movement of the coupling elements relative to one another beyond the locking position. The spring bridge sits on a lateral exterior side of the holder and is shaped so that a force, in particular a compressive force, can be applied manually to the spring bridge, said force acting transversely to the longitudinal extent and opposite the spring action of the spring bridge, for displacement of the second coupling element out of the locking position and into the release position. The holder may include a rotating shaft on which the quick coupling is situated on one free end and on which a handle part is provided in a T shape on an opposite end. Another aspect of a solution to the problem according to the invention thereupon consists of a combination of a novel holder, as indicated, and at least one medical instrument that can be secured releasably in the holder and has the features of an instrument shaft which has a connecting end, such that an undercut is formed on the connecting end of the instrument shaft; as well as corresponding advantageous refinements of the instrument having a conically widening thickened area having a conical shape from the free end of the instrument shaft in the remaining course pointing away from the free end, this thickened area dropping back on its end section facing away from the free end, forming the undercut on a smaller circumference of the instrument shaft; and that parallel flattened areas forming the opposing faces are formed on the connecting end of the instrument shaft.

Thus, according to the invention, a novel holder for a medical, in particular a surgical instrument has a quick coupling for accommodating a connecting end having an undercut on an instrument shaft of the medical instrument. The quick coupling has a first coupling element having a first axial through-hole for the connecting end. It also has a second coupling element having a second axial through-hole for the connecting end. The first and second coupling elements can be moved relative to one another in a direction transversely to the axial direction of the through-hole, out of a locked position, in which the first and second through-holes are offset relative to one another in such a way that one edge of the second through-hole engages lockingly in an undercut on the connecting end of the instrument shaft and into a released position, in which at least the first and second axial through-holes are aligned with one another, so that the connecting end can be passed freely through both through-holes. Further, according to the invention the first and second coupling elements are connected to one another in one piece via a spring bridge, and the spring bridge pre-stresses the first and second coupling elements relative to one another into the locked position.

In such an embodiment of the holder in its quick coupling, this first eliminates the requirement to provide small part and separate locking elements such as locking balls. The locking effect is achieved only through the offset of the two through-holes in the first and second coupling elements, which they have assumed to one another in the locked position as a normal position because of the pre-stress, in a direction transversely to the axial extent. In other words, a medical instrument which is guided with the connecting end of its instrument shaft through the first through-hole is first secured through this through-hole in the radial direction. Axially securing and/or locking it is then accomplished by the connecting end also protruding through the second through-hole wherein the second through-hole is shifted transversely to the axial direction with respect to the first through-hole such that it lies with its edge in contact with an undercut on the connecting end, engaging beneath it and thereby locking the instrument shaft in the axial direction. As already mentioned above, in this locked position, there may still be a certain axial play. Frequently such axial play is even desired by the users with manually operated holders because this provides additional tactile assistance. In other cases, for example, in instruments for drilling through hard bone in the area of the skull, such an axial play is necessary because a rotational engagement of a drive is possible only in a position of the instrument shaft in which it is displaced axially toward the rear, this position being assumed against a spring load and impressing the instrument against the skull to be drilled, but when a hole has been drilled in the skull, this position is relaxed, the spring stops the rotary drive and thus disengages the drill. This prevents the drill drive from continuing and injuring the soft tissue parts or even the brain situated beneath the skull.

Another advantage of the holder according to the invention is that it is formed in one piece in its connection between the first and second coupling elements. This also eliminates possibly breaking it down into individual small parts, as would be necessary in cleaning and sterilizing the holder. Furthermore, with the corresponding, and in particular preferred, design and embodiment of the holder, in particular its quick coupling, corresponding interspaces are created between the elements that are connected to one another in one piece, these elements being readily accessible, cleanable and then sterilizable with the appropriate cleaning instruments. Thus, extremely narrow interspaces in particular, such as those which occur on ball bearing surfaces of locking balls, for example, and are hardly completely accessible in cleaning and sterilization or adequately accessible for a thorough cleaning and sterilization, can be avoided.

On the whole, the quick coupling may advantageously be designed in one piece and is preferably made of an easily sterilizable material, which also has adequate biocompatibility for surgical use, such as in particular a medically tolerable stainless steel. Use of such a metal (titanium or titanium alloys or other metals that may be used medically might also be considered) is also advantageous because with this kind of material with a comparatively thin-walled construction, allows a sufficient restoring force in the direction of the spring bridge forming the locked position in a one-piece connection between the first and second coupling elements.

The holder according to the invention may also advantageously have in its quick coupling locking structures for interacting with mating structures on the connecting end of the instrument shaft for a rotation-proof arrangement of the instrument in the holder. Such an embodiment is relevant in particular when rotational forces and/or torques are to be transferred to the medical instrument for example in the case of a drill or a reamer. One possible design for forming such locking structures consists of arranging side jaws on the quick coupling on an exterior front side of the first coupling element, on opposing sides of the through-hole passing through the surface on the front side, these side jaws protruding outward from the surface on the front side and having parallel planar contact surfaces facing one another and forming the locking structures. These contact surfaces are provided for contact with the mating surfaces that form the connecting end of the instrument shaft.

In a preferred embodiment of the holder according to the invention, the quick coupling has a base body on which the first and second coupling elements are integrally molded, in particular being formed in one piece therewith, a recess being provided in the base body, bordered on one side by a wall of the base body and along which the spring bridge extends on one side opposite the wall and, at an angle thereto, the second coupling element also extends. This embodiment is a design variant that has a particularly simple design and has a structure that is simple to form, while at the same time meeting the requirements of easy cleanability and sterilizability of the holder, in particular in the area of its quick coupling, because in particular when the recess is designed with large enough dimensions, the interspace between the wall of the base body and the spring bridge having large enough dimensions for insertion of cleaning instruments, this section can be cleaned and sterilized easily. The recess may, but need not necessarily, also be at an angle, so that its course may in particular follow the angular shape of the course of the spring bridge and of the second coupling element, which is at an angle thereto.

Furthermore, according to an advantageous embodiment variant of the holder according to the invention, it may be advantageous if the recess has a setback and the second coupling element has a protrusion (the opposite design is of course also possible, i.e., a protrusion on the recess and the setback on the coupling element), which together form a stop that prevents a movement of the coupling elements relative to one another that goes beyond the locking position. Such a stop prevents errors during operation and, on the whole, increases the stability and reliability of the holder according to the invention.

According to another advantageous embodiment of the invention, the spring bridge may lie on a lateral exterior side of the holder and may be designed so that a force, in particular a compressive force that acts manually on the spring bridge, across its longitudinal extent and opposite the spring action of the spring bridge, may be applied for displacing the second coupling element out of the locking position and into the release position. In other words, the spring bridge here is at the same time a "pressure switch" which, when actuated, may result in the position of the first and second coupling elements relative to one another being transferred out of the locking position and into the release position, so that, in this position, in particular an instrument connected to the holder is released from the holder, and optionally also an instrument with the connecting end of the instrument shaft is inserted into the quick coupling of the holder and secured there.

The holder may in particular be a manually operable holder having a rotating shaft on which the quick coupling is arranged on its free end, and on which furthermore, a handle part is arranged in a T shape on an end opposite the free end. However, the invention is not limited to such a holder. A holder according to the invention may also be implemented in differently shaped designs that may be operated manually, just as it may also be implemented as a component of a motor-operated instrument drive, whether a drive that is operated axially or a rotationally operated drive.

In another aspect of the invention, it consists of a combination of a holder, as described in greater detail above, and at least one medical, in particular surgical instrument, which can be attached releasably to the holder and includes an instrument shaft having a connecting end, an undercut being formed on the connecting end of the instrument shaft. This combination is not limited to a holder and a single instrument but may also include a set consisting of one or more holders and one or more medical instruments.

With such a combination, it may be advantageous if, as indicated according to an advantageous embodiment of the invention, the instrument has a thickened area on the connecting end of its instrument shaft, said thickened area becoming wider conically in its remaining course away from the free end and dropping back on its end section facing away from the free end, thus forming the undercut, to a smaller extent of the instrument shaft. This conical thickened area serves to facilitate insertion of the connecting end of the instrument shaft into the quick coupling, because due to the conical section, the second coupling element of the quick coupling is displaced out of the locking position and moved into the release position when a compressive force directed axially is applied to the instrument shaft until reaching the undercut situated behind the cone, the diameter of the instrument shaft dropping off and the second coupling element snapping into the locking position.

For a transfer of rotational forces and/or torques, it is advantageous if the instrument of such a combination has parallel flattened areas forming the mating surfaces on its connecting end of the instrument shaft.

BRIEF DESCRIPTION OF THE DRAWINGS

Additional advantages and features of the invention are derived from the following description of one exemplary embodiment on the basis of the accompanying figures, in which:

FIG. 1 shows one exemplary embodiment of a holder according to the invention for a medical, in particular surgical, instrument in a perspective diagram, obliquely from a side having the quick coupling;

FIG. 2 shows the holder from FIG. 1 in a side view with a view of a side face of the quick coupling;

Figure 3:
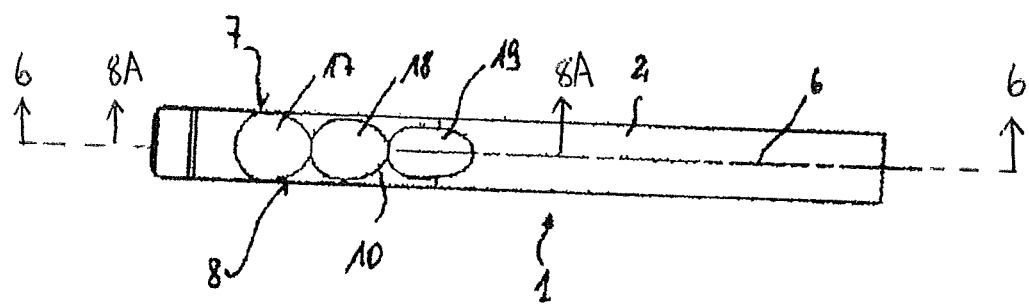
FIG. 3 shows the holder from FIG. 1 in a side diagram with a view of a first narrow side.
Figure 4:
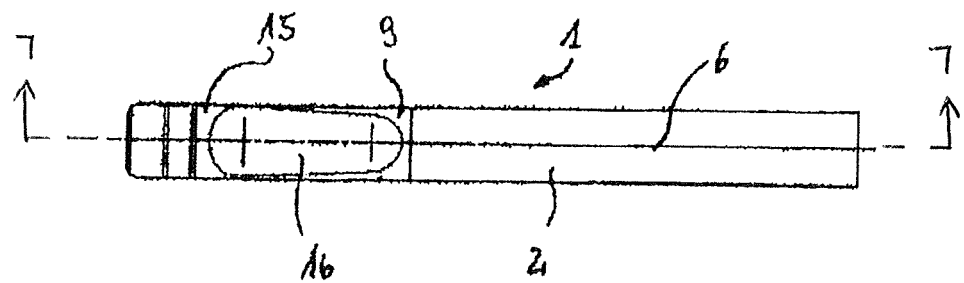
FIG. 4 shows the holder from FIG. 1 in a side diagram with a view of another narrow side opposite the narrow side shown in FIG. 3.

The figures show an exemplary embodiment of a holder according to the invention, which is explained in greater detail below. The figures are not to be regarded as complete construction drawings but instead are limited to diagramming the features of the exemplary embodiment of a holder according to the invention that are essentially to the invention as well as other relevant features.

A holder according to the invention for a medical, in particular surgical instrument is shown in various (partial) views in the figures and is labeled with reference numeral 1 in general.

Method(s) of Implementing the Invention

The holder 1 in this exemplary embodiment has an elongated shape having a shaft section 2. A quick coupling 3 is integrally molded on a front end of this shaft section 2, serving to accommodate a connecting end of an instrument shaft of the medical instrument having an undercut, wherein the holder is to be connected to this holder.

The quick coupling 3 has a main body 26 and on its front side has a receiving hole 5, which is in the shape of a drill hole guided along a longitudinal axis 6 of the holder 1. The quick coupling 3 is formed in one piece in particular and has two flattened side faces 7 and 8 as well as narrow sides 9 and 10 running between them, running apart from one another, opening in a wedge shape, to a section near the front side 4, from which the narrow sides 9, 10 taper again. The narrow sides 9, 10 develop into two protrusions 11 and/or 12 protruding on the front side 4.

A coupling plate 13 is shaped by corresponding cutouts from the one-piece material of the quick coupling 3 and is connected at one end to a spring bridge 15, which is separated by a slot 14 from the main body 26 of the quick coupling 3. In a region axially opposite the front side 4, where the slot 14 ends, the spring bridge 15 is connected in one piece to the main body 26 of the quick coupling 3. The spring bridge 15 has a flattened area 16 on its surface situated on the narrow side 9, said flattened area being designed as an ergonomic and/or haptic element for contact with the thumb on one hand. Recessed grips 17, 18, 19 are formed on the opposite narrow side 10. These are provided for contact with the fingers, in particular the index finger, the middle finger and the ring finger of the hand, the thumb of which is resting in the flattened area 16. The spring tongue 14 can thus be deflected by one hand in the direction of the opposite narrow side 10 to cause a longitudinal displacement of the coupling plate 13 in the same direction. The coupling plate 13 and spring bridge 15 are connected to one another in one piece, as already mentioned, and form an angle, such that the coupling plate 13 runs essentially perpendicular to the longitudinal axis 6 and the direction in which the receiving hole 5 passing along this axis is drilled. The coupling plate 13 sits in a receiving slot 27, which is formed in the quick coupling 3, more specifically in its main body 26, and runs at an angle to the slot 14. The coupling plate 13 can move in one longitudinal direction in the receiving slot 27. The receiving slot 27 and the slot 14 are situated at an angle to one another and jointly form an approximately L-shaped slot.

Figure 5:
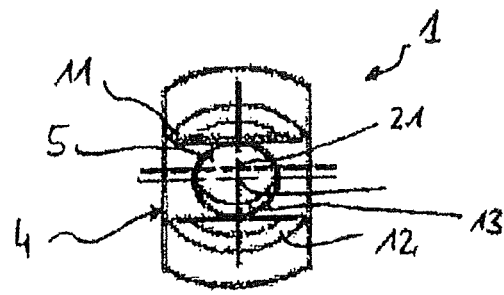
FIG. 5 shows a front view of the holder according to FIG. 1 from the coupling side of the quick coupling in an enlarged diagram.
Figure 6:
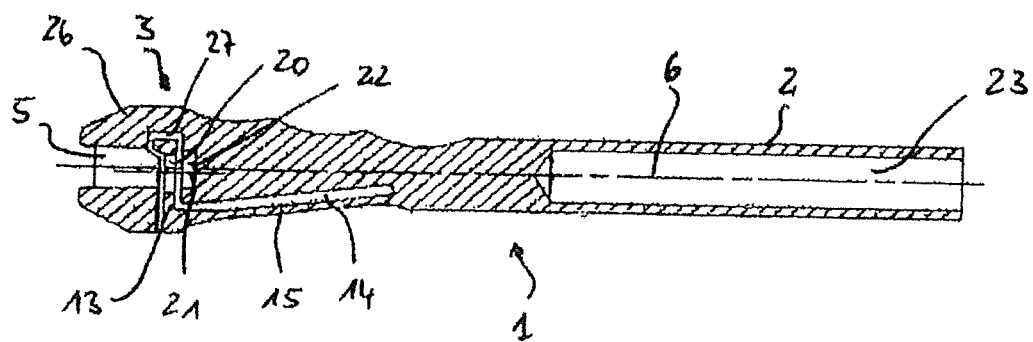
FIG. 6 shows a longitudinal sectional diagram through the holder taken along line 6-6 of FIG. 3.

As shown in FIG. 6 in particular, a through-hole 20 is formed in the coupling plate 13. This through-hole 20 also runs axially in its extent, i.e., with a direction of extent parallel to the longitudinal axis 6, but in the position shown in FIG. 6, in which the spring bridge 15 can be seen in a starting position and/or a resting position, with its central axis 21 offset relative to the longitudinal axis 16, which forms the central axis of the receiving hole 5 at the same time. The receiving hole 5 extends beyond the section in which the coupling plate 13 traverses it, up to an end section 22. This can also be seen in the front view according to FIG. 5, which shows the offset axes, the central axis 21 and the longitudinal axis 6, as well as a section of the coupling plate 13, which can be seen with a view of the receiving hole 5 through this hole.

Figure 9:
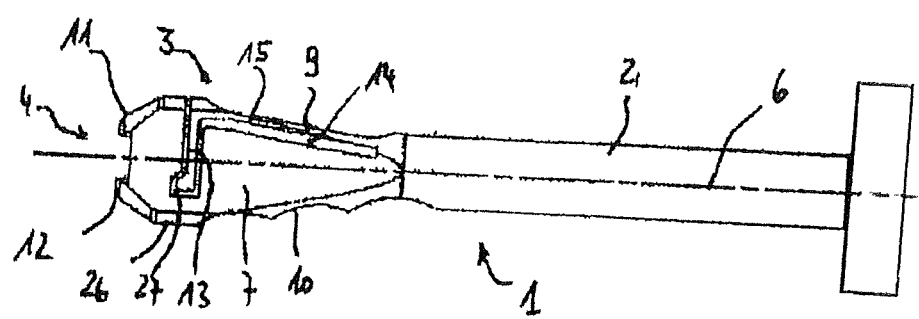
FIG. 9 shows the holder of FIG. 2 with a T-shaped handle.

FIG. 6 also shows that a receptacle 23, designed as a blind hole, is formed in the shaft section 2 of the holder 1 and according to the invention serves to connect the holder 1 to additional structures, for example, the drive shaft of the motorized instrument drive to rotary drive or to a T-bar handle (FIG. 9) formed transversely to the longitudinal extent of the holder 1, i.e., transversely to the longitudinal axis 6, in particular perpendicular to the same.

Figure 7:
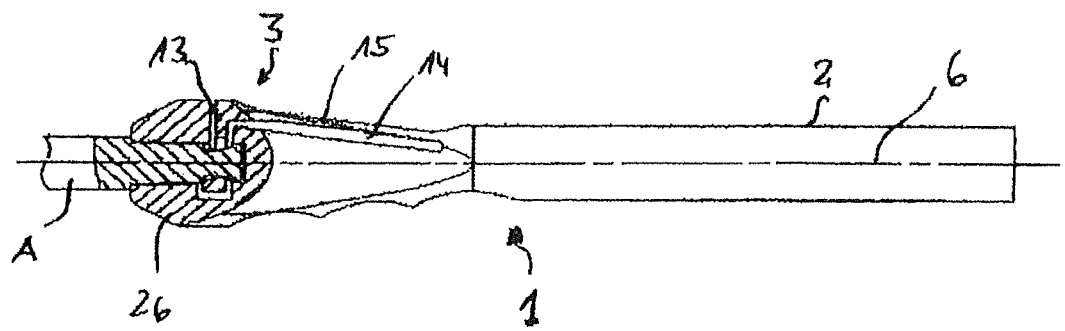
FIG. 7 shows the holder with the connecting end of a medical instrument accommodated therein in a partially sectional diagram taken along line 7-7 of FIG. 4.

The quick coupling 3 of the holder 1 according to the invention is equipped for connection to a connecting end A (cf. FIG. 7) of an instrument shaft. In the construction and design shown here, the quick coupling 3 and/or the connecting end 8 is/are formed as a so-called Hudson connection and/or a corresponding connecting coupling in particular.

The procedure in connecting the connecting end A to the quick coupling 3 of the holder 1 is illustrated again separate in the three diagrams and drawings in FIGS. A1, 8B and 8C and is described below on the basis of these diagrams.

Figure 8A:
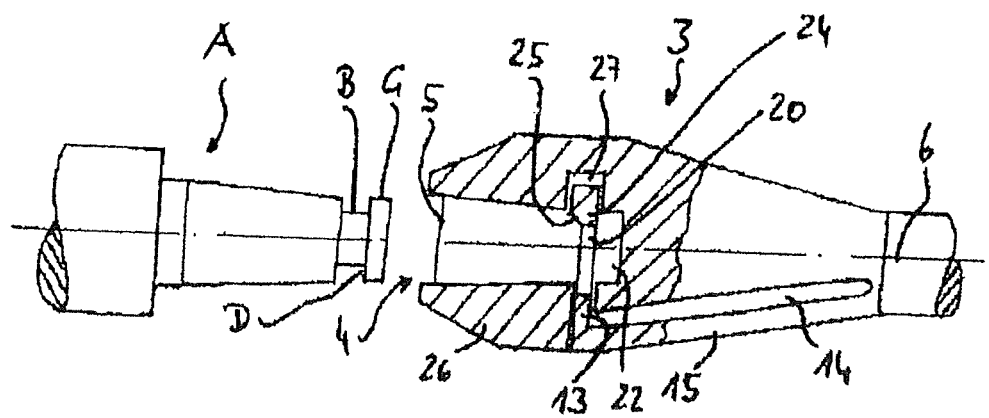
FIGS. 8A, 8B and 8C show the section of the holder taken along line 8A-8A of FIG. 3, having the quick coupling enlarged in the three diagrams 8A through 8C, during insertion of a connecting end of a medical instrument for securing the same on the holder.

In a first starting condition illustrated in FIG. 8A, the quick coupling 3 of the holder is shown with the spring bridge 15 in a relaxed starting position and/or resting position. In this position the receiving hole 5 and the through-hole 20 in the coupling plate 13 are not aligned precisely. Instead a section 24 of the coupling plate 13 bordering the through-hole 20 protrudes into the region of the receiving hole 5 and in particular covers the end section 22 thereof to this extent. As shown in this enlarged diagram (FIG. 8A), the coupling plate 13 is provided with a starting angle 25 facing the front side 4 in the section 24.

Figure 8B:
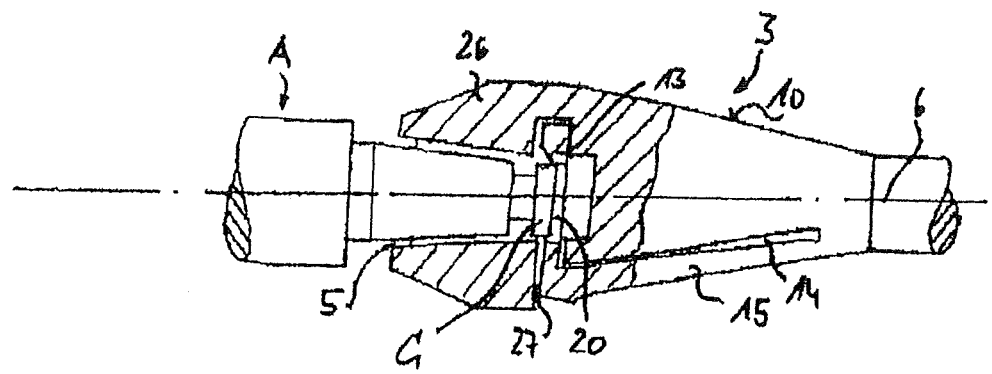
Figure 8C:
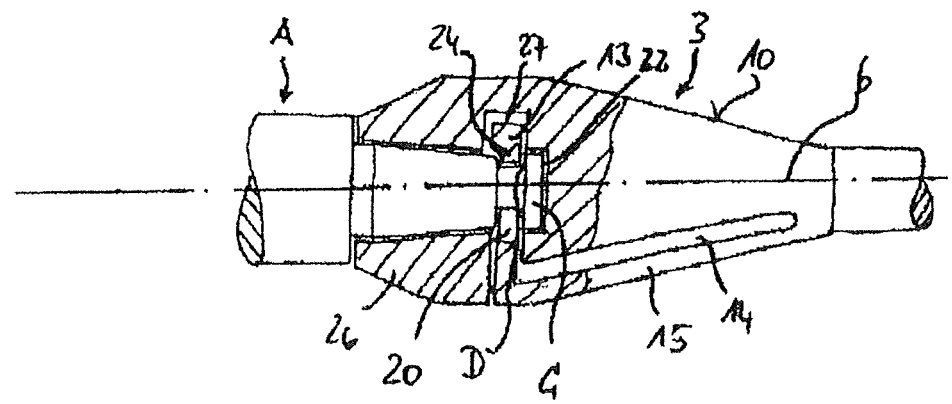

The connecting end A of the instrument shaft has a region B of a tapering diameter on its free end and has an end section C covering the former. An undercut D is formed on this section. If as shown in FIG. 8B the connecting end A is then inserted into the receiving hole 5, then the end section C abuts against the starting angle 25 of the coupling plate 13. In this way, the coupling plate 13 is forced upward in the graphical diagram, i.e., in the direction of the narrow side 10. Because of the elasticity and flexibility of the spring bridge 15, the coupling plate 13 gives in this direction, so that the through-hole 20 can be passed by the end section C. If the effect of the starting angle 25 in conjunction with the end section C is not sufficient to allow the coupling plate 13 to yield in the direction of the narrow side 10 so that the through-hole 20 is passable for the end section C, then it is possible to remedy this manually by pressing the spring-bridge 15 in the direction of the opposing narrow side 10 while closing the slot 14.

If the end section C has passed completely through the through-hole 20 in the coupling plate 13, it enters the end section 22 of the receiving hole 5, and the coupling plate 13, driven by the spring force of the spring bridge 15, can snap back into its resting position and/or starting position. In this position the section 24 which is in contact with the connecting end A via the undercut D locks the connecting end A in the axial direction, i.e., in the direction of the longitudinal axis 6 of the holder. To release the connecting end out of this position, the spring bridge 15 must be pressed in the direction of the opposite narrow side 10 so that the coupling plate 13 is shifted, so that the through-hole 20 is exposed for passage of the end section C and the connecting A can be removed.

It has become clear from the preceding discussion of the exemplary embodiment that the quick coupling 6 of the holder according to the invention has a simple design due to the cooperation of through-hole 5 and through-hole 20 in cooperation with the spring bridge 15 and the corresponding locking function, and furthermore, due to the preferred one-piece design. Therefore, in addition to a simple and robust operability, this yields in particular easy cleanability and sterilizability after use. The exemplary embodiment shown here does not restrict the invention, which is defined in its broad scope in the following patent claims.

LIST OF REFERENCE NUMERALS

1 Holder
2 Shaft section
3 Quick coupling

4 Front side
5 Receiving hole
6 Longitudinal axis
7 Side face
8 Side face
9 Narrow side
10 Narrow side
11 Protrusion
12 Protrusion
13 Coupling plate
14 Slot
15 Spring bridge
16 Flattened area
17 Recessed grip
18 Recessed grip
19 Recessed grip
20 Through-hole
21 Central axis
22 End section
23 Receptacle
24 Section
25 Starting angle
26 Main body
27 Receiving slot
A Connecting end
B Region
C Concluding [section]
D Undercut

The invention claimed is:

1. A holder for a medical instrument that has an instrument shaft with a connecting end having an undercut formed therein; said holder comprising:
a base body having an outer wall and a recess defined in the outer wall; wherein the recess is generally L-shaped and includes a slot and a receiving slot; wherein the receiving slot is oriented perpendicular to a longitudinal axis of the base body;
a quick coupling provided on the base body and adapted to accommodate the connecting end of the instrument shaft, wherein the quick coupling comprises:
a first coupling element;
a second coupling element; and
a spring bridge; wherein the first coupling element, the second coupling element and the spring bridge are integrally formed with the base body thereby forming a monolithic component;
wherein the first coupling element and the second coupling element are connected to one another via the spring bridge; and wherein at least a portion of the spring bridge is separated from a remaining portion of the base body by the slot;
wherein the first coupling element defines a first axial through-hole;
wherein the second coupling element sits in the receiving slot and the second coupling element defines a second axial through-hole; wherein the second coupling element is movable relative to the first coupling element in a direction transverse to an axial direction of the first and second through-holes out of a locking position in which the first and second through-holes are offset relative to one another in such a manner that one edge of the second through-hole is adapted to lockingly engage in the undercut on the connecting end of the instrument shaft; and into a release position in which the first through-hole and the second through-hole are aligned at least to such an extent that the first and second through-holes are adapted to permit the connecting end of the instrument shaft to pass freely through the first and second through-holes, and wherein the spring bridge prestresses the first coupling element and the second coupling element into the locking position relative to one another.

2. The holder according to claim 1, wherein the quick coupling further comprises locking structures adapted to cooperate with mating structures on the connecting end of the instrument shaft for a twist-proof arrangement of the medical instrument in the holder.

3. The holder according to claim 2, further comprising side jaws provided on an exterior front side of the first coupling element, wherein the side jaws are arranged on opposite sides of the first through-hole, and wherein the side jaws pass through a surface on the front side of the first coupling element and protrude outward from the surface, wherein the side jaws have mutually parallel planar contact surfaces facing one another; and wherein the contact surfaces are adapted to contact the mating structures on the connecting end of the instrument shaft.

4. The holder according to claim 1, wherein the recess defined in the base body is bordered by a wall of the base body on one end, wherein the spring bridge extends on a side opposite the wall and the second coupling element extends at an angle relative to the first coupling element.

5. The holder according to claim 4, wherein the recess has a setback, and the second coupling element has a protrusion, and wherein the setback and protrusion together form a stop which prevents any movement of the first and second coupling elements relative to one another beyond the locking position.

6. The holder according to claim 1, wherein the spring bridge sits on a lateral exterior side of the holder and is shaped so that when a force acting transversely to a longitudinal axis of the base body and opposite a spring action of the spring bridge is manually applied to the spring bridge, said force deforms the spring bridge and moves the second coupling element out of the locking position and into the release position.

7. The holder according to claim 1, wherein the base body further includes a rotatable shaft having a free end and an opposite end; wherein the quick coupling is situated on the free end of the shaft and a handle part is provided in a T-shape on the opposite end of the shaft.

8. The holder according to claim 1, wherein the first coupling element and the second coupling element are connected to one another in a monolithic design via the spring bridge and wherein a portion of each of the first coupling element and the second coupling element are in direct and continuous contact with the spring bridge.

9. The holder according to claim 1, wherein the slot of the L-shaped recess is oriented at an angle relative to the longitudinal axis of the base body.

10. The holder according to claim 1, further comprise a shaft section that extends rearwardly from the base body in a direction opposite to a front of the base body.

11. The holder according to claim 1, wherein the base body has a front, a top, a bottom and opposing sides; wherein the top, bottom and sides extend rearwardly from the front; and wherein the base body tapers from a maximum height proximate the front of the base body and moving rearwardly away from the front; and wherein the height is measured from the top to the bottom of the base body.

12. The holder according to claim 1, wherein the base body has a front, a top, a bottom and opposing sides; wherein the spring bridge is located adjacent the top; and wherein the base body further comprises a plurality of spaced-apart recesses defined in the bottom.

13. The holder according to claim 12, the slot and receiving slot are defined in the sides of the base body.

14. The holder according to claim 1, wherein the outer wall of the base body comprises a front, a top, a bottom and two sides, where the top, bottom and sides extend rearwardly from the front; and wherein a section of each of the top and bottom of the base body extend forwardly and inwardly beyond the front of the base body; and wherein each section forms a projection that is located adjacent the first axial hole defined in the front of the base body.

15. The holder according to claim 1, wherein the spring bridge and the second coupling element are substantially L-shaped when viewed from a side of the base body.

16. A combination comprising:
a medical instrument having an instrument shaft with a connecting end, wherein the connecting end has an undercut formed thereon;
a holder comprising:
a base body;
a quick coupling provided on the base body for accommodating the connecting end of the instrument shaft, wherein the quick coupling has:
a first coupling element and a second coupling element;
a spring bridge connecting the first coupling element and the second coupling element to one another, wherein the first coupling element, the second coupling element and the spring bridge are integral with the base body thereby forming a monolithic component;
wherein the first coupling element defines a first axial through-hole; and
wherein the second coupling element defines a second axial through-hole, wherein the second coupling element is movable relative to the first coupling element in a direction transverse to the axial direction of the through-holes out of a locking position;
wherein the first and second through-holes are offset relative to one another in such a manner that one edge of the second through-hole lockingly engages in the undercut on the connecting end of the instrument shaft, into a release position, wherein the first axial through-hole and the second axial through-hole are aligned at least to such an extent that the first axial through-hole and the second axial through-hole permit the connecting end of the instrument shaft to pass freely through the first and second through-holes, and wherein the spring bridge pre-stresses the first coupling element and the second coupling element into the locking position relative to one another; and wherein the medical instrument is detachably attachable to the holder.

17. The combination according to claim 16, wherein the medical instrument further comprises a conically widening thickened area having a conical shape from a free end of the instrument shaft wherein a remaining part of the thickened area points away from the free end, and wherein the thickened area drops back on an end section facing away from the free end and forms the undercut on a smaller circumference on the connecting end of the instrument shaft.

18. The combination according to claim 16, further comprising parallel flattened areas formed on the connecting end of the instrument shaft and wherein the flattened areas comprise opposing faces on the connecting end.

19. The combination as defined in claim 16, wherein the medical instrument is a surgical instrument.

20. The combination as defined in claim 16, wherein the base body has an outer wall and a recess is defined in the outer wall; wherein the recess is generally L-shaped and includes a slot and a receiving slot; wherein the receiving slot is oriented perpendicular to a longitudinal axis of the base body and the second coupling element is received in the receiving slot.

* * * * *